(12) United States Patent
Slayton et al.

(10) Patent No.: US 9,907,942 B2
(45) Date of Patent: Mar. 6, 2018

(54) METHODS AND SYSTEMS FOR MODULATING MEDICANTS USING ACOUSTIC ENERGY

(71) Applicant: Guided Therapy Systems, LLC, Mesa, AZ (US)

(72) Inventors: Michael H. Slayton, Tempe, AZ (US); Peter G. Barthe, Phoenix, AZ (US)

(73) Assignee: GUIDED THERAPY SYSTEMS LLC, Mesa, AZ (US)

( * ) Notice: Subject to any disclaimer, the term of this patent is extended or adjusted under 35 U.S.C. 154(b) by 330 days.

(21) Appl. No.: 14/868,923

(22) Filed: Sep. 29, 2015

(65) Prior Publication Data

US 2016/0015954 A1 Jan. 21, 2016

Related U.S. Application Data

(63) Continuation of application No. 12/116,810, filed on May 7, 2008, now Pat. No. 9,216,276.
(Continued)

(51) Int. Cl.
*A61M 37/00* (2006.01)
*A61N 7/02* (2006.01)
(Continued)

(52) U.S. Cl.
CPC .......... *A61M 37/0092* (2013.01); *A61N 7/02* (2013.01); *A61B 8/4281* (2013.01);
(Continued)

(58) Field of Classification Search
CPC ...... A61N 7/00; A61N 7/02; A61N 2007/004; A61N 2007/008; A61N 2007/0052;
(Continued)

(56) References Cited

U.S. PATENT DOCUMENTS

| | | | | |
|---|---|---|---|---|
| 4,379,145 A | * | 4/1983 | Masuho | C07K 16/303 530/389.7 |
| 4,668,516 A | * | 5/1987 | Duraffourd | A61K 8/37 424/770 |

(Continued)

*Primary Examiner* — Kevin C Sirmons
*Assistant Examiner* — William Carpenter
(74) *Attorney, Agent, or Firm* — Quarles & Brady LLP

(57) ABSTRACT

This invention provides methods and systems uniquely capable of enhancing medicant delivery and/or effectiveness through the use of energy to predictably disrupt membranes and mechanically and thermally modulate cells and tissues. In exemplary embodiments, the methods and systems disclosed herein are capable of modulating multiple layers of tissue. In an exemplary embodiment, the energy is acoustic energy (e.g., ultrasound). In other exemplary embodiments, the energy is photon based energy (e.g., IPL, LED, laser, white light, etc.), or other energy forms, such radio frequency electric currents, or various combinations of acoustic energy, electromagnetic energy and other energy forms or energy absorbers such as cooling. Medicants can be first introduced to the region of interest by diffusion, circulation, and/or injection. An exemplary system for enhancing medicant delivery and/or effectiveness comprises a control system, a probe, and a display or indicator system. Imaging and/or monitoring may alternatively be coupled and/or co-housed with an ultrasound system contemplated by the present invention.

20 Claims, 12 Drawing Sheets

Related U.S. Application Data

(60) Provisional application No. 60/916,509, filed on May 7, 2007.

(51) Int. Cl.
  *A61N 7/00* (2006.01)
  *A61B 8/00* (2006.01)
  *A61B 90/00* (2016.01)

(52) U.S. Cl.
  CPC .......... *A61B 2090/378* (2016.02); *A61M 2037/0007* (2013.01); *A61M 2205/3375* (2013.01); *A61N 7/00* (2013.01); *A61N 2007/0008* (2013.01); *A61N 2007/0043* (2013.01); *A61N 2007/0056* (2013.01)

(58) Field of Classification Search
  CPC ...... A61N 2007/0056; A61N 2007/006; A61N 2007/0065; A61N 2007/0069; A61N 2007/0073; A61N 2007/0078; A61N 2007/0082; A61N 2007/0086; A61N 2007/0091

See application file for complete search history.

(56) References Cited

U.S. PATENT DOCUMENTS

| | | | | |
|---|---|---|---|---|
| 4,938,217 | A * | 7/1990 | Lele | A61N 7/02 601/3 |
| 5,460,595 | A * | 10/1995 | Hall | A61B 8/546 310/316.01 |
| 5,814,599 | A * | 9/1998 | Mitragotri | A61B 5/14514 424/450 |
| 6,135,971 | A * | 10/2000 | Hutchinson | A61N 7/02 601/3 |
| 6,623,430 | B1 * | 9/2003 | Slayton | A61B 5/01 600/439 |
| 2002/0040199 | A1 * | 4/2002 | Klopotek | A61N 7/00 601/3 |
| 2003/0212129 | A1 * | 11/2003 | Liu | A61K 31/375 514/474 |

* cited by examiner

US 9,907,942 B2

METHODS AND SYSTEMS FOR MODULATING MEDICANTS USING ACOUSTIC ENERGY

CROSS-REFERENCE TO RELATED APPLICATIONS

This application is a continuation of U.S. patent application Ser. No. 12/116,810 filed May 7, 2008, now U.S. Pat. No. 9,216,509, which claims benefit of U.S. Provisional Patent Application 60/916,509 filed May 7, 2007, each of which are incorporated in its entirety by reference, herein.

BACKGROUND OF THE INVENTION

Skin comprises at least four distinct layers of tissue: the nonviable epidermis (i.e., the stratum corneum), the viable epidermis, the dermis, and subcutaneous connective tissue and fat. The circulatory system lies in the dermis and tissues below the dermis. As skin generally prohibits the transport of macromolecules to the dermis and tissues below the dermis, needles are often required to administer macromolecular medicants.

Ultrasound has long been used for diagnostic imaging applications. More recently however, several new therapeutic applications for ultrasound are being discovered. Among the applications for ultrasound, enhanced transdermal medicant delivery and/or effectiveness has received considerable attention. To date, however, the better part of ultrasound-enhanced medicant delivery and/or effectiveness efforts have been focused on ultrasound at frequencies below 200 kHz, and prior systems have directed ultrasound at single layers of tissue.

SUMMARY OF THE INVENTION

This invention improves upon the prior art by providing methods and systems uniquely capable of enhancing medicant delivery and/or effectiveness through the use of energy (e.g., acoustic energy). An exemplary embodiment predictably disrupts membranes and mechanically and thermally modulates cells and tissues. In exemplary embodiments, the methods and systems disclosed herein are capable of modulating multiple layers of tissue (e.g., a plurality of depths within a cell membrane or tissue).

The methods and systems disclosed herein contemplate delivering focused, unfocused, and/or defocused ultrasound energy to a region of interest at various spatial and temporal energy settings, in the range of about 100 kHz to about 500 MHz. In an exemplary embodiment, the energy is acoustic energy (e.g., ultrasound). In other exemplary embodiments, the energy is photon based energy (e.g., IPL, LED, laser, white light, etc.), or other energy forms, such radio frequency electric currents, or various combinations of acoustic energy, electromagnetic energy and other energy forms or energy absorbers such as cooling.

Medicants can be first introduced to the region of interest by diffusion, circulation, and/or injection, to name a few. In other embodiments, the methods and systems disclosed herein are configured to interact with chemicals naturally occurring or already existing within the body in terms of, for example, concentration, function, and cell division properties.

An exemplary system for enhancing medicant delivery and/or effectiveness comprises a control system, a probe, and a display or indicator system. The probe can comprise various probe and/or transducer configurations. In an exemplary embodiment, the probe delivers focused, unfocused, and/or defocused ultrasound energy to the region of interest. Imaging and/or monitoring may alternatively be coupled and/or co-housed with an ultrasound system contemplated by the present invention.

The control system and display system can also comprise various configurations for controlling probe and system functionality, including for example, a microprocessor with software and a plurality of input/output devices, a system for controlling electronic and/or mechanical scanning and/or multiplexing of transducers, a system for power delivery, systems for monitoring, systems for sensing the spatial position of the probe and/or transducers, and systems for handling user input and recording treatment results, among others.

In accordance with an exemplary embodiment, a coupling agent, comprised of at least one of a gel, cream, liquid, emulsion or other compound, is used to couple the probe to a patient's body. In an exemplary embodiment, the coupling agent contains medicants that are delivered to the patient's body during the emission of energy from the probe.

BRIEF DESCRIPTION OF THE DRAWINGS

The subject matter of the invention is particularly pointed out and distinctly claimed in the concluding portion of the specification. The invention, however, both as to structure and method of operation, may best be understood by reference to the following description taken in conjunction with the claims and the accompanying drawing figures, in which like parts may be referred to by like numerals, and:

DETAILED DESCRIPTION

Figure 1A:
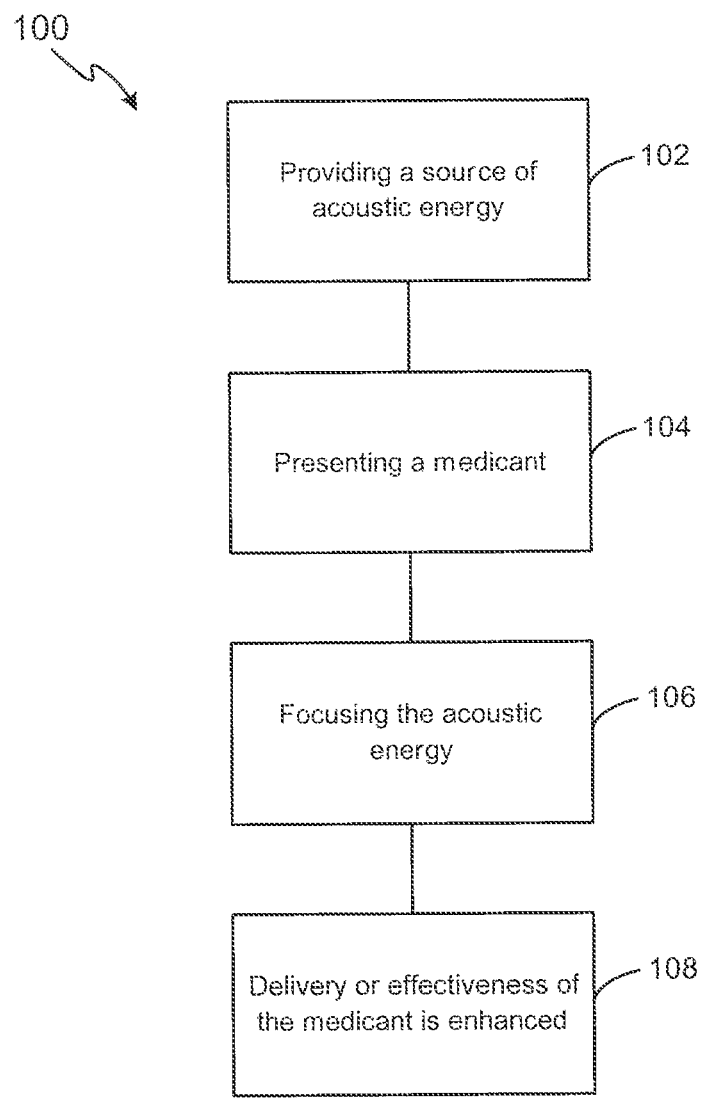
FIG. 1A illustrates a block diagram of a method for modulating medicants in accordance with an exemplary embodiment of the present invention.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and the exemplary embodiments relating to methods and systems for using acoustic energy to enhance medicant delivery and effectiveness, as described herein, are merely indicative of exemplary applications for the invention. For example, the principles, features and methods discussed may be applied to any medical application, e.g., the methods and systems described herein can be used in combination with any coagulative therapies. Further, various aspects of the present invention may be suitably applied to other applications.

Disclosed is an exemplary method of modulating cells and tissues to enhance medicant delivery and/or effectiveness that comprises delivering energy to a region of interest (ROI) within one or more layers of tissue. In an exemplary embodiment, the energy is acoustic energy (e.g., ultrasound in the range of about 100 kHz to about 500 MHz, more preferably in the range of about 100 kHz to about 20 MHz, and most preferably in the range of about 200 kHz to about 20 MHz). In other exemplary embodiments, the energy is photon based energy (e.g., IPL, LED, laser, white light, etc.), or other energy forms, such radio frequency electric currents, or various combinations of acoustic energy, electromagnetic energy and other energy forms or energy absorbers such as cooling. In yet other exemplary embodiments, combinations of acoustic and photon based energy sources can be used, e.g., pre-treating with photon-based energy and then use of ultrasound energy alone or simultaneously with the photon-based energy, or any other combinations for modulating cells and tissues to enhance medicant delivery and/or effectiveness.

An exemplary method of modulating cells and tissues produces numerous predictable mechanical and thermal physiological effects at a ROI. For example, an exemplary method is predictable in terms of precision and accuracy in targeting and focusing energy at desired three dimensional coordinates within a cell membrane or tissue or a plurality of cell membranes and tissues and at various spatial and temporal energy settings. For example, because cells are on the order of micrometers, and cell membrane thickness is on the order of nanometers, to target an individual cell or membrane would require a very high or extreme frequency, thus a plurality is useful in exemplary embodiments. In an exemplary embodiment ultrasound, photon based or radio frequency (electromagnetic) treatment is provided to artificial or engineered tissues, such as artificial skin or organs, or stem cell derived tissues.

Providing ultrasound energy to cell membranes or tissues can enhance drug delivery and/or effectiveness in numerous ways. For example, the permeability and/or transparency of cell membranes can be modulated. For example, in some embodiments, the permeability and/or transparency of cell membranes is increased. Heating can cause better diffusion of drugs through the layers of skin tissue. Cavitation and radiation force involves sustained oscillatory motion of bubbles (aka stable cavitation) and/or rapid growth and collapse of bubbles (aka inertial cavitation). Resulting fluid velocities, shear forces and shock waves can disrupt cell membranes or tissues and induce chemical changes in the surrounding medium. The collapse of bubbles can additionally increase the bubble core temperature and induce chemical changes in the medium (e.g., generate highly reactive species, such as free radicals). Each of the above effects can impact drug delivery and effectiveness. In addition, other ways to impact drug delivery include melting or mechanically disrupting thermally sensitive or mechanically fragile medicant-carrying liposomes and/or other chemical loaded, gas or liquid filled stabilized spheres, analogous to local delivery.

For example, drug delivery can be enhanced when shock waves generated upon collapse of bubbles disrupt the stratum corneum and thereby enhance skin permeability. Likewise, drug effectiveness can be enhanced when shock waves transiently compromise the integrity of cell membranes or tissues, or when local free-radical concentration enhances medicant toxicity. Moreover, certain medicants can be activated and/or released using energy. In that regard, a medicant encapsulated in a carrier can be released at the site of interest using energy (e.g., acoustic energy). Consider for example, U.S. Pat. No. 6,623,430, entitled "Method and Apparatus for Safely Delivering Medicants to a Region of Tissue Using Imaging, Therapy and Temperature Monitoring Ultrasonic System", and co-pending U.S. patent application Ser. No. 08/943,728, entitled "Method and Apparatus for Safely Delivering Medicants to a Region of Tissue Using Ultrasound", both of which are hereby incorporated by reference.

In various exemplary embodiments, the ROI is located within one of the nonviable epidermis (i.e., the stratum corneum), the viable epidermis, the dermis, the subcutaneous connective tissue and fat, and the muscle. Depths may be in the range of about 0 mm to about 60 mm, 80 mm, or 100 mm or more. In accordance with an exemplary embodiment, the ROI is located about 20 mm to about 30 mm below the stratum corneum. Further, while only one ROI is depicted, a plurality of ROI can be treated, and in some embodiments, simultaneously. For example, the ROI may consist of one or more organs or a combination of tissues either superficial or deep within the body.

This method and system is uniquely capable of disrupting cell membranes or tissues and inducing chemical changes in the surrounding medium at either a single or multiple layers of skin tissue simultaneously (e.g., a plurality of depths within a cell membrane or tissue simultaneously). For example, one frequency of acoustic energy at one skin layer might generate shock waves upon collapse of bubbles to disrupt the stratum corneum and thereby enhance skin permeability. A different frequency of acoustic energy at a different skin layer might simply provide heat to cause better diffusion of medicants through the layers of skin tissue. Yet another frequency of acoustic energy at a different skin layer might compromise the integrity of cell membranes or tissues, or generate local free-radicals to enhance or reduce medicant toxicity. In an exemplary embodiment, acoustic energy is deposited in three-dimensions and at variable depths to selectively increase tissue permeability to thereby steer or guide the medicant through the tissue to a region of interest.

For example, and with reference to FIG. 1A, an exemplary embodiment provides a method 100 for enhancing medicant delivery and/or effectiveness comprising the steps of: providing a source of acoustic energy 102; presenting a medicant to a cell membrane or tissue 104; and focusing the acoustic energy from the source to a plurality of depths within the cell membrane or tissue 106, wherein the acoustic energy is in the range of about 100 kHz to about 500 MHz, wherein the plurality of depths are each in the range of about 0 mm to about 100 mm; and wherein the delivery and/or effectiveness of the medicant is enhanced 108.

Yet another exemplary embodiment provides a method for delivering a medicant to a region of interest within a cell membrane or tissue comprising the steps of: providing a source of acoustic energy; presenting a medicant to the cell membrane or tissue; focusing the acoustic energy from the source to a first depth within the cell membrane or tissue, wherein the acoustic energy has a first spatial and temporal energy profile; and focusing the acoustic energy from the source to a second depth within the cell membrane or tissue, wherein the acoustic energy has a second spatial and temporal energy profile; and wherein the medicant is delivered to the region of interest.

Medicants can be first introduced to a region of interest orally, by diffusion upon application to the skin, circulation following entry into the circulatory system, direct injection thereto, to name a few. That said, introduction may occur either in or not in direct contact with the circulatory system. For example, in some exemplary embodiments, the methods and systems disclosed herein affect chemicals naturally occurring or already existing within the body (e.g., cells, amino acids, proteins, antibodies, minerals, vitamins, etc.) in terms of, for example, concentration, function, and cell division properties. In one exemplary embodiment, the method and system disclosed herein "spur" or catalyze cellular processes, for example cell growth.

In accordance with exemplary embodiments, a coupling agent, comprised of at least one of a gel, cream, liquid, emulsion solid, composite or other compound, is used to couple the probe to a patient's body. In an exemplary embodiment, the coupling agent contains medicants that are delivered to the patient's body during the emission of energy from the probe.

In accordance with an aspect of an exemplary embodiment, the medicant is also used to couple a probe to the skin. Therefore, the medicant can have multiple uses. First, the medicant is used to couple the probe to the skin. Second, since the medicant contains drugs and other medicines, the same are delivered to the skin when energy is applied from the probe (e.g, via sonophoresis).

In an exemplary embodiment, the medicines and drugs within the medicant are used for skin treatment. Therefore, as the patient is being treated by the application of energy at non-ablative levels, therapeutic drugs are also being administered to the patient to treat skin disorders.

Figure 1B:
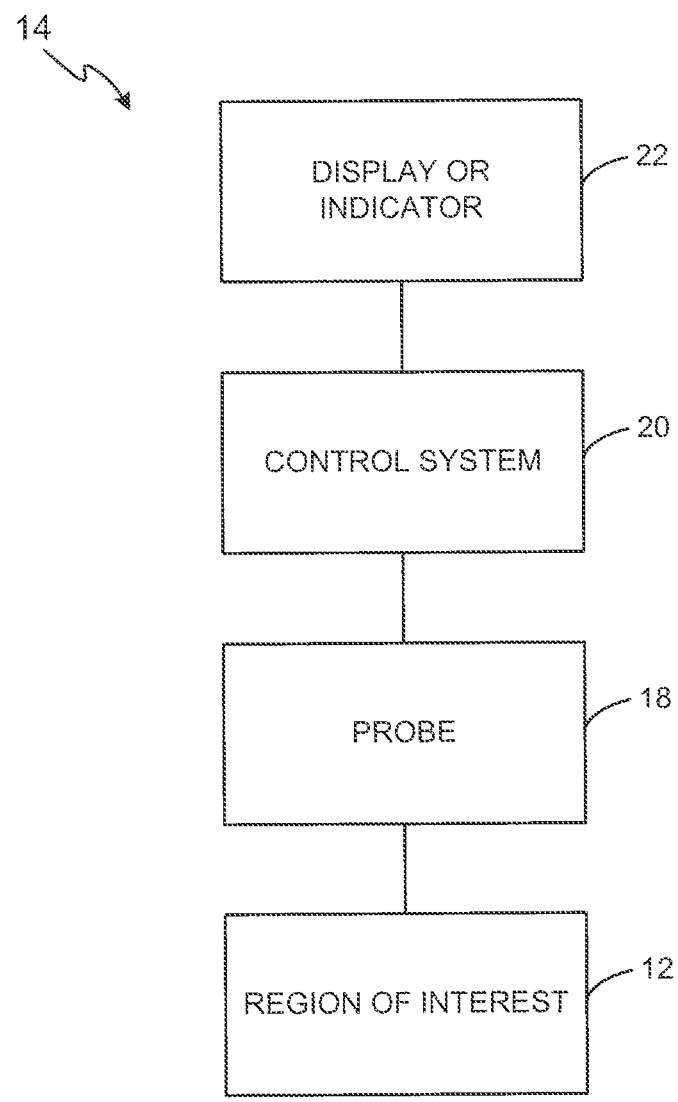
FIG. 1B illustrates a block diagram of a system for modulating medicants in accordance with an exemplary embodiment of the present invention.

An exemplary system 14 for modulating cells and tissues to enhance medicant delivery and/or effectiveness is provided and depicted in FIG. 1B. An exemplary system 14 comprises a display or indicator 22, a control system 20, and a probe 18.

Display system can be any type of system that conveys images or information apart from images about system 14 or ROI 12 to the user. Therefore, display system 22 can be a computer monitor, television screen or it can be a simply type of indicator system such a liquid crystal display or light emitting diode display in various exemplary embodiments. Liquid crystal displays and light emitting diode displays are particularly useful when system 14 is a hand-held system.

Figure 2:
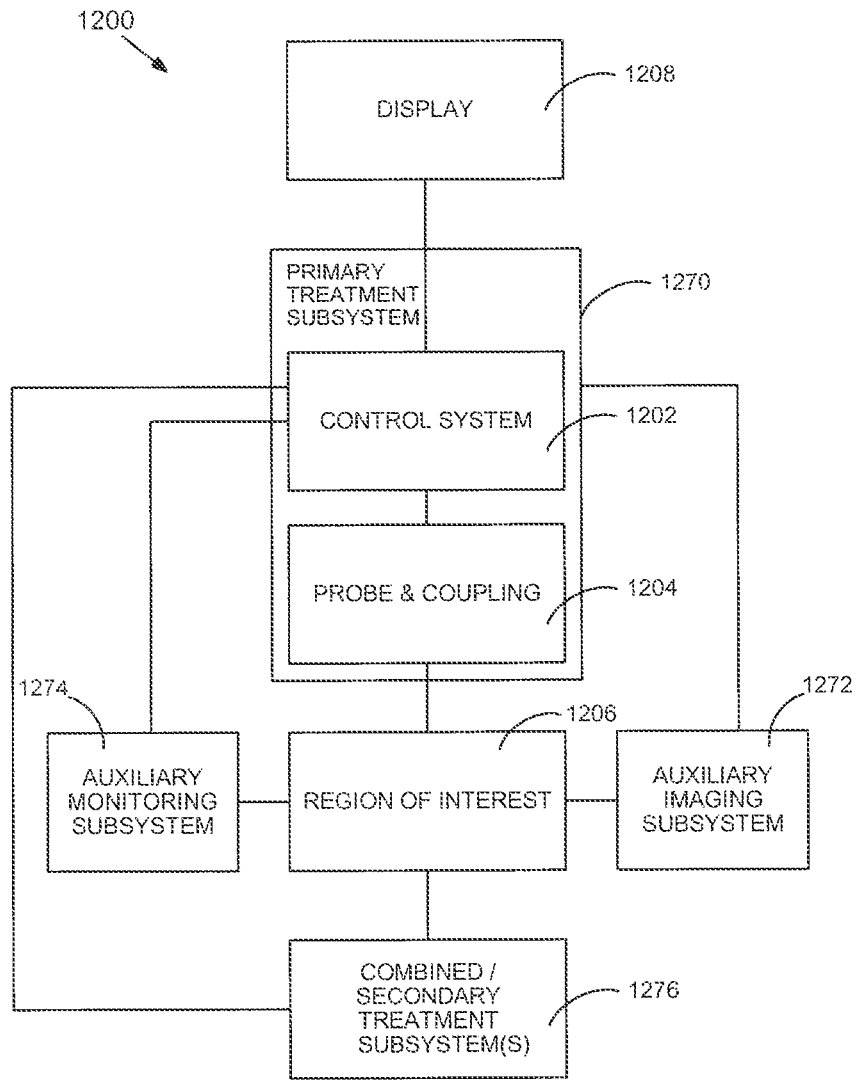
FIG. 2 illustrates a block diagram of a treatment system comprising an ultrasound treatment subsystem combined with additional subsystems and methods of treatment monitoring and/or treatment imaging as well as a secondary treatment subsystem in accordance with an exemplary embodiment of the present invention.

In accordance with another exemplary embodiment, with reference to FIG. 2, an exemplary treatment system 1200 can be configured with and/or combined with various auxiliary systems to provide additional functions. For example, an exemplary treatment system 1200 for treating a region of interest 1206 can comprise a control system 1202, a probe 1204, and a display 1208. Treatment system 1200 further comprises one or more of an auxiliary imaging modality 1274 and/or one or more of an auxiliary monitoring or sensing modality 1272, which may be based upon at least one of photography and other visual optical methods, magnetic resonance imaging (MRI), computed tomography (CT), optical coherence tomography (OCT), electromagnetic, microwave, or radio frequency (RF) methods, positron emission tomography (PET), infrared, ultrasound, acoustic, or any other suitable method of visualization, localization, or monitoring within region-of-interest 1206, including imaging/monitoring enhancements. Such imaging/monitoring enhancement for ultrasound imaging via probe 1204 and control system 1202 could comprise M-mode, persistence, filtering, color, Doppler, and harmonic imaging among others; furthermore an ultrasound treatment system 1270, as a primary source of treatment, may be combined with a secondary source of treatment 1276, including radio frequency (RF) energy, microwave energy, or other photon based energy methods including intense pulsed light (IPL), laser, infrared laser, microwave, or any other suitable energy source. A multi-modality coupler analogous to FIG. 1B is a particularly useful embodiment for a multi-modality treatment, sensing, monitoring and imaging system.

Figure 3:
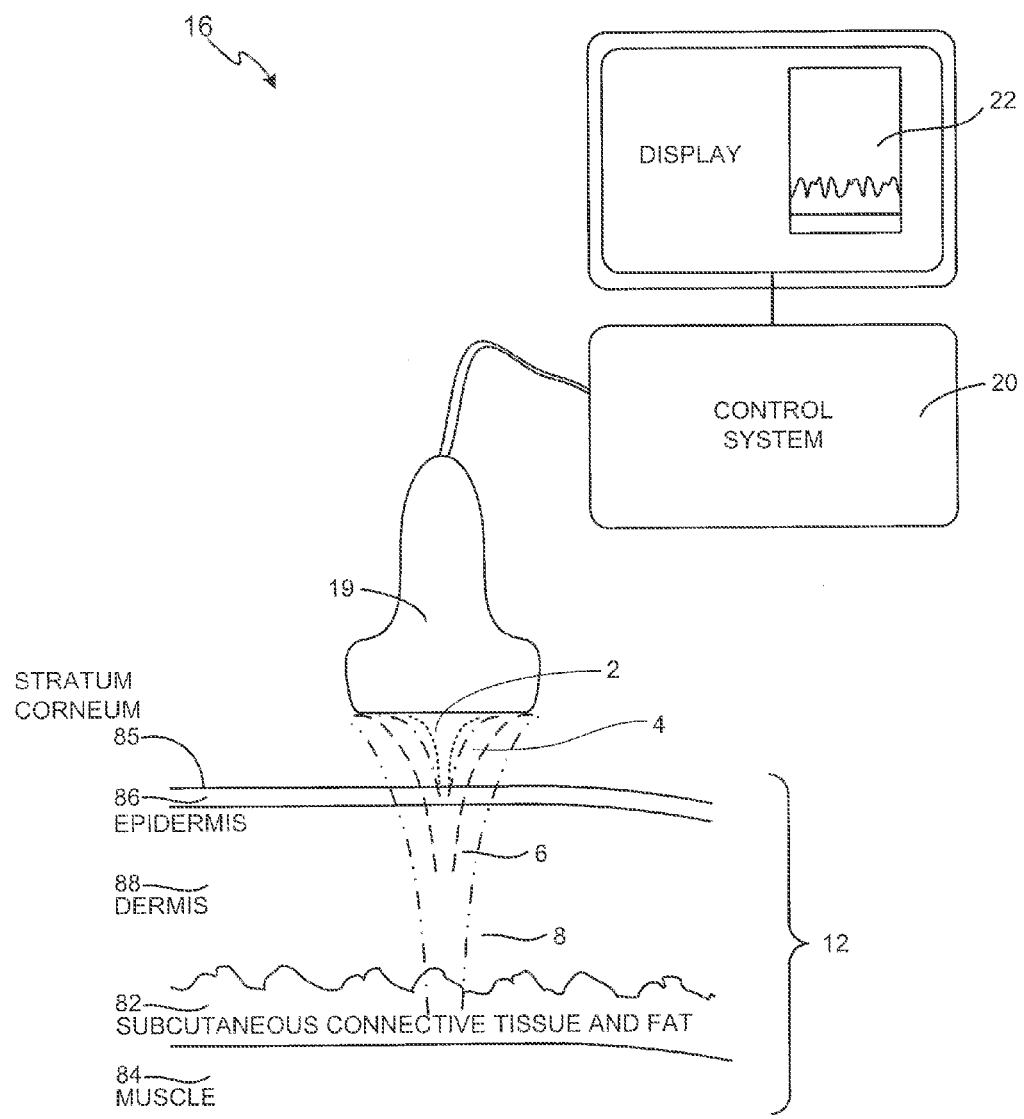
FIG. 3 illustrates a schematic diagram of a system for modulating medicants in accordance with an exemplary embodiment of the present invention.

In an exemplary embodiment, with reference to FIG. 3, an exemplary system 16, comprising a display 22, a control system 20, a transducer 19, is used to deliver energy 2, 4, 6, and/or 8 to and monitor ROI 12, within one or more of stratum corneum 85, viable epidermis 86, dermis 88, subcutaneous connective tissue and fat 82, and muscle 84. Other exemplary systems are disclosed in co-pending U.S. patent application Ser. No. 10/950,112 entitled "Method and System For Combined Ultrasound Treatment", which is hereby incorporated by reference.

With continued reference to FIG. 3, an exemplary transducer 19 is a transducer that delivers ultrasound energy 2, 4, 6 and/or 8 to ROI 12. In some embodiments, a fluid filled or gel couple is used to couple transducer 19 to a patient's body. In some embodiments, an additional coupling is necessary and/or multiple fluid filled or gel couples are used, each having distinct acoustic properties.

In another exemplary embodiment, suction is used to attach transducer 19 to the patient's body. In this exemplary embodiment, a negative pressure differential is created and transducer 19 attaches to stratum corneum 85 by suction. A vacuum-type device is used to create the suction and the vacuum device can be integral with, detachable, or completely separate from transducer 19. The suction attachment of transducer 19 to stratum corneum 85 and associated negative pressure differential ensures that transducer 19 is properly coupled to stratum corneum 85. Further, the suction-attachment also reduces the thickness of the tissue to make it easier to reach distinct layers of tissue.

With additional reference to FIG. 3, ultrasound energy 2, 4, 6 and/or 8 can be emitted in various energy fields. Energy fields can be focused, unfocused, defocused, and/or made substantially planar by transducer 19 to provide a plurality of different effects. Energy can be applied at one or more points in one or more C-planes or C-scans by automated or manual movement. For example, a substantially planar energy field can provide a therapeutic and/or pretreatment effect, a focused energy field can provide a more intense therapeutic effect, and a non-focused energy field can provide a more mild therapeutic effect. It should be noted that the term "non-focused" as used throughout, is meant to encompass energy that is unfocused or defocused.

An exemplary transducer 19 emits ultrasound energy for imaging, or treatment, or a combination of both imaging and treatment. In an exemplary embodiment, transducer 19 is configured to emit ultrasound energy at specific depths in ROI 12, as described below. In this exemplary embodiment of FIG. 3, transducer 19 emits unfocused or defocused ultrasound energy over a wide area in ROI 12 for treatment purposes.

Figure 4A:
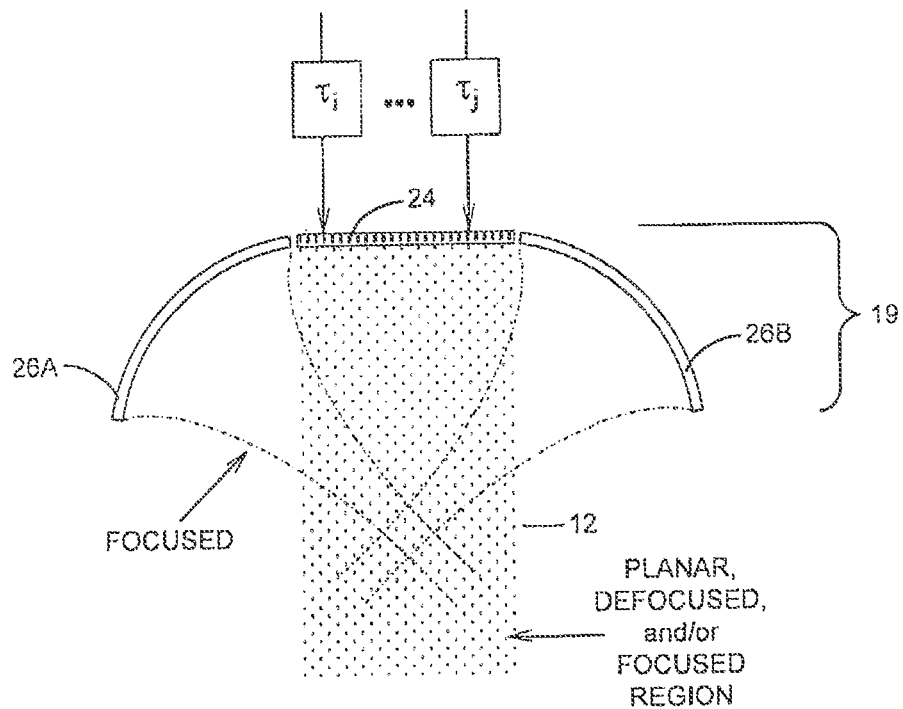
FIGS. 4A, 4B, 4C, 4D and 4E illustrate cross-sectional diagrams of an exemplary transducer in accordance with various embodiments of the present invention.
Figure 4B:
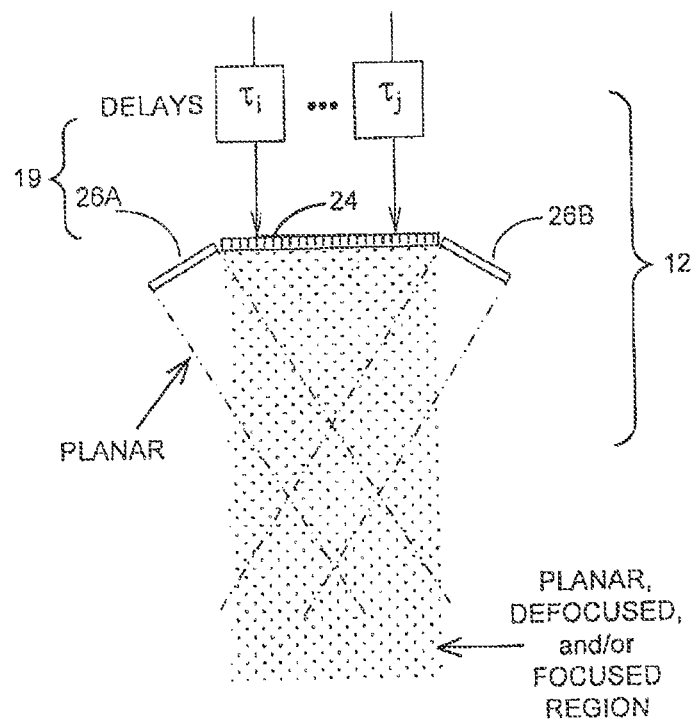

With reference to FIGS. 4A and 4B, transducer 19 can comprise one or more transducers configured for facilitating treatment. Transducer 19 can also comprise one or more transduction elements, e.g., elements 26A or 26B. The transduction elements can comprise a piezoelectrically active material, such as lead zirconante titanate (PZT), or any other piezoelectrically active material, such as a piezoelectric ceramic, crystal, plastic, and/or composite material, as well as lithium niobate, lead titanate, barium titanate, and/or lead metaniobate. In addition to, or instead of a piezoelectrically active material, transducer 19 can comprise any other materials configured for generating radiation and/or acoustical energy. Transducer 19 can also comprise one or more matching and/or backing layers configured along with the transduction elements such as coupled to the piezoelectrically active material. Transducer 19 can also be configured with single or multiple damping elements along the transduction elements.

In accordance with an exemplary embodiment, the thickness of the transduction elements of transducer 19 can be configured to be uniform. That is, the transduction elements can be configured to have a thickness that is substantially the same throughout. In accordance with another exemplary embodiment, the transduction elements can also be configured with a variable thickness, and/or as a multiple damped device. For example, the transduction elements of transducer 19 can be configured to have a first thickness selected to provide a center operating frequency of a lower range, for example from approximately 1 kHz to 3 MHz. Transduction element 26 can be configured with a second thickness selected to provide a center operating frequency of a higher range, for example from approximately 3 to 100 MHz, or more.

Transducer 19 can be configured as a single broadband transducer excited with at least two or more frequencies to provide an adequate output for raising the temperature within ROI 12 to a desired level. Transducer 19 can also be configured as two or more individual transducers, wherein each transducer 19 comprises transduction elements, the thickness of which may be selected as above to provide a desired center operating frequency.

Moreover, in an exemplary embodiment, any variety of mechanical lenses or variable focus lenses, e.g. liquid-filled lenses, may also be used to additionally focus and or defocus the energy field. For example, with reference to exemplary embodiments depicted in FIGS. 4A and 4B, transducer 19 may also be configured with an electronic focusing array 24 in combination with one or more transduction elements to facilitate increased flexibility in treating ROI 12. Array 24 may be configured in a manner similar to transducer 19. That is, array 24 can be configured as an array of electronic apertures that may be operated by a variety of phases via variable electronic time delays, for example, $T_i \ldots T_j$. By the term "operated," the electronic apertures of array 24 may be manipulated, driven, used, and/or configured to produce and/or deliver energy in a manner corresponding to the phase variation caused by electronic time delays. For example, these phase variations can be used to deliver defocused beams, planar beams, and/or focused beams, each of which may be used in combination to achieve different physiological effects in ROI 12.

Transduction elements may be configured to be concave, convex, and/or planar. For example, in an exemplary embodiment depicted in FIG. 4A, transduction elements 26A and 26B are configured to be concave in order to provide focused energy for treatment of ROI 12. Additional embodiments are disclosed in U.S. patent application Ser. No. 10/944,500, entitled "System and Method for Variable Depth Ultrasound Treatment", incorporated herein by reference. In an exemplary embodiment of FIG. 4A transduction elements 24 and associated time or phase delays are perpendicular to that shown in FIG. 4A, whereby such perpendicularly disposed transduction elements 24 are therapy, imaging, or dual-mode imaging-therapy elements.

In another exemplary embodiment, depicted in FIG. 4B, transduction elements 26A and 26B can be configured to be substantially flat in order to provide substantially uniform energy to ROI 12. In an exemplary embodiment of FIG. 4B transduction elements 24 and associated time or phase delays are perpendicular to that shown in FIG. 4B, whereby such perpendicularly disposed transduction elements 24 are therapy, imaging, or dual-mode imaging-therapy elements. While FIGS. 4A and 4B depict exemplary embodiments with the transduction elements configured as concave and substantially flat, respectively, the transduction elements can be configured to be concave, convex, and/or substantially flat. In addition, the transduction elements can be configured to be any combination of concave, convex, and/or substantially flat structures. For example, a first transduction element can be configured to be concave, while a second transduction element within transducer 19 can be configured to be substantially flat.

Figure 4C:
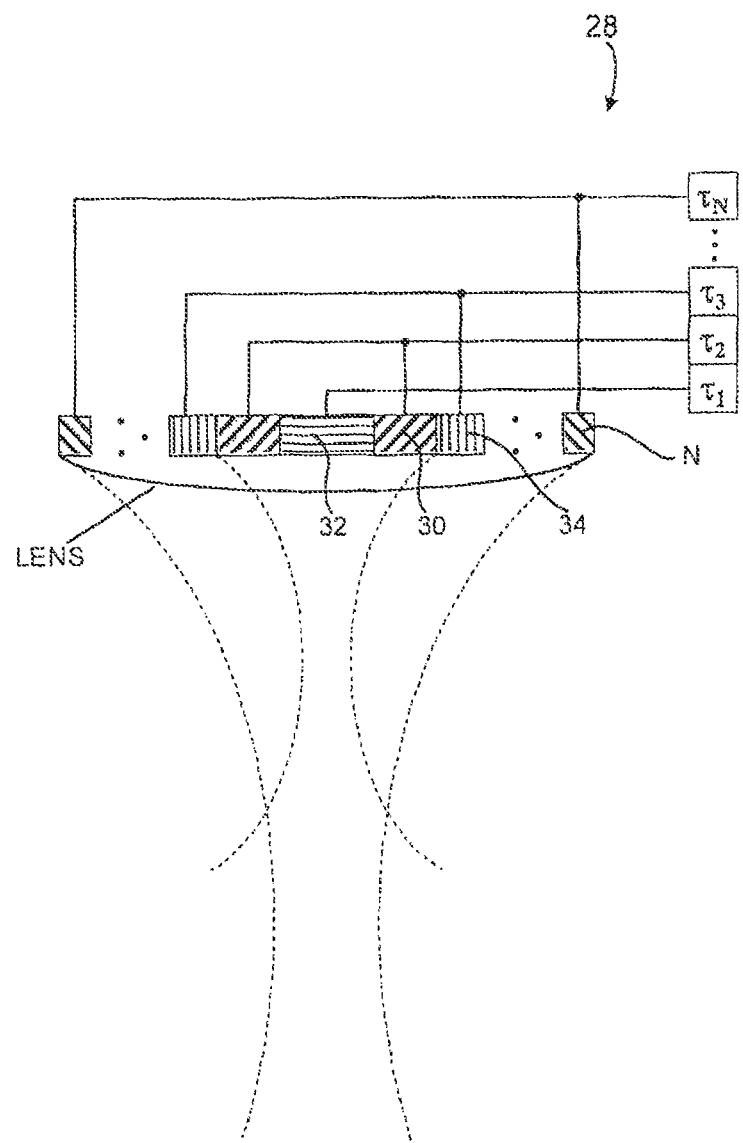
Figure 4D:
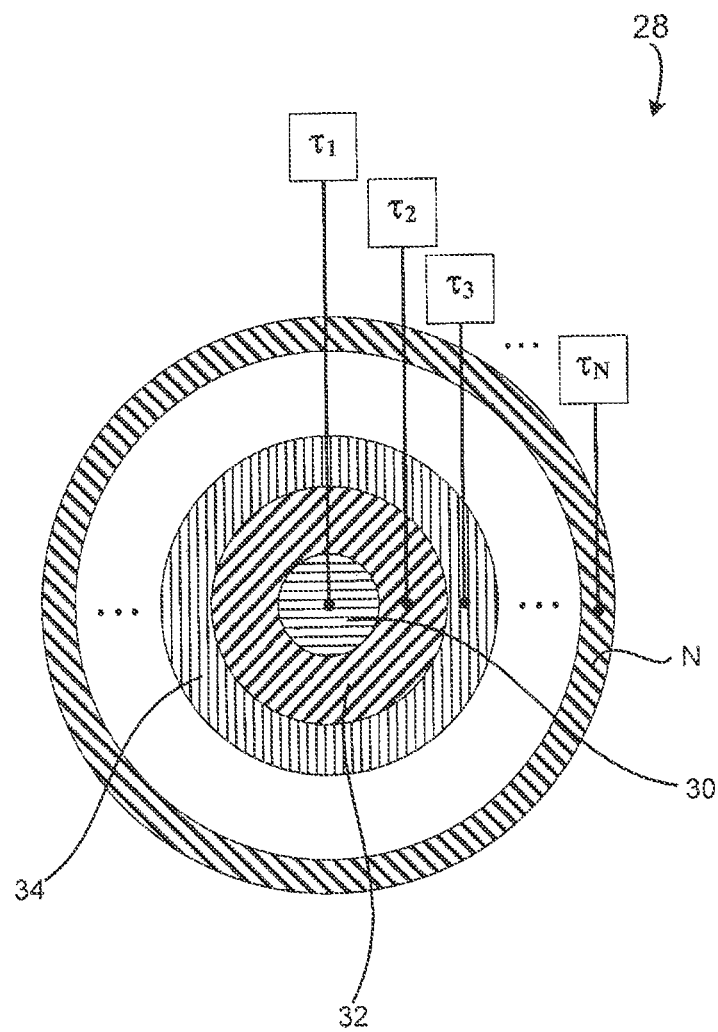

With reference to FIGS. 4C and 4D, transducer 19 can also be configured as an annular array to provide planar, focused and/or non-focused acoustical energy. For example, in accordance with an exemplary embodiment, an annular array 28 can comprise a plurality of rings 30, 32, 34 to N. Rings 30, 32, 34 to N can be mechanically and electrically isolated into a set of individual elements, and can create planar, focused, or non-focused waves. For example, such waves can be centered on-axis, such as by methods of adjusting corresponding transmit and/or receive delays, $T_1, T_2, T_3 \ldots T_N$. An electronic focus can be suitably moved along various depth positions, and can enable variable strength or beam tightness, while an electronic defocus can have varying amounts of defocusing. In accordance with an exemplary embodiment, a lens and/or concave, convex, and/or substantially flat shaped annular array 28 can also be provided to aid focusing or defocusing such that any time differential delays can be reduced. Movement of annular array 28 in one, two or three-dimensions, or along any path, such as through use of probes and/or any conventional robotic arm mechanisms, may be implemented to scan and/or treat a volume or any corresponding space within ROI 12.

Figure 4E:
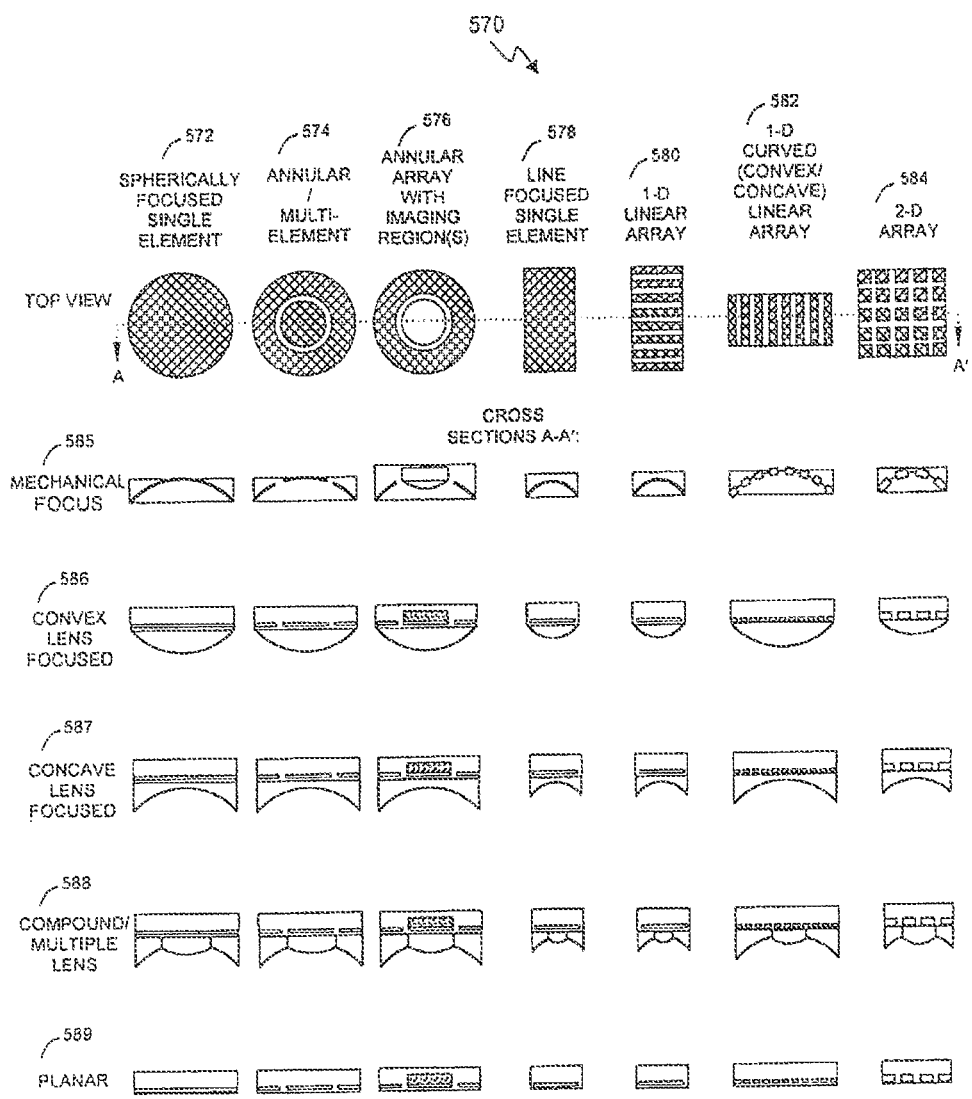

With reference to FIG. 4E, an exemplary transducer 570 can also be configured as a spherically focused single element 572, annular/multi-element 574, annular array with imaging region(s) 576, line focused single element 578, 1-D linear array 580, 1-D curved (convex/concave) linear array 582, and/or 2-D array 584, with mechanical focus 585, convex lens focus 586, concave lens focus 587, compound/multiple lens focus 588, and/or planar array form 589, to achieve focused, unfocused, or non-focused sound fields for both imaging and/or therapy. Other lens shapes can still be used in other exemplary embodiments of the present invention. Analogous to spherically focused single element 572 to be configured for multiple annulii 574 and/or imaging regions 576, an exemplary embodiment for the therapeutic line-focused single element 578, and 1-D and 2-D arrays 580, 582 and 584 is to dispose one or more imaging elements or imaging arrays in their aperture, such as along the center of their aperture. In general a combination of imaging and therapy transducers or dual mode imaging-therapy transducers can be utilized.

Figure 5A:
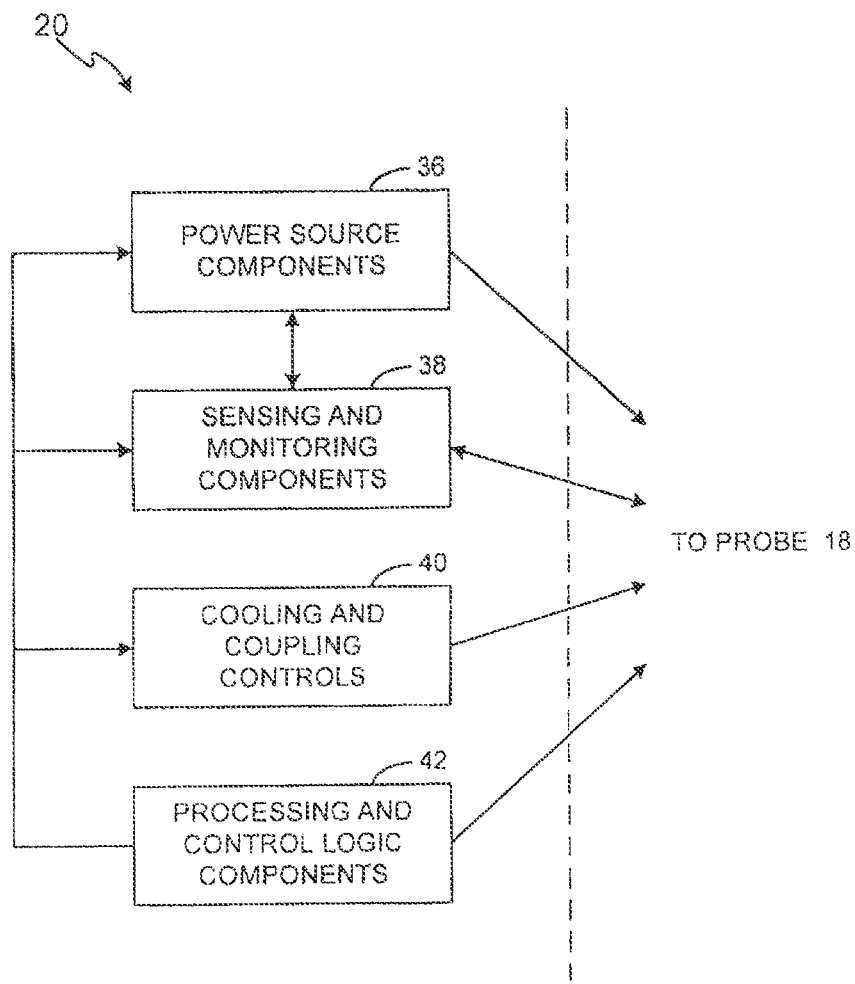
FIGS. 5A, 5B, and 5C illustrate block diagrams of an exemplary control system in accordance with exemplary embodiments of the present invention.
Figure 5B:
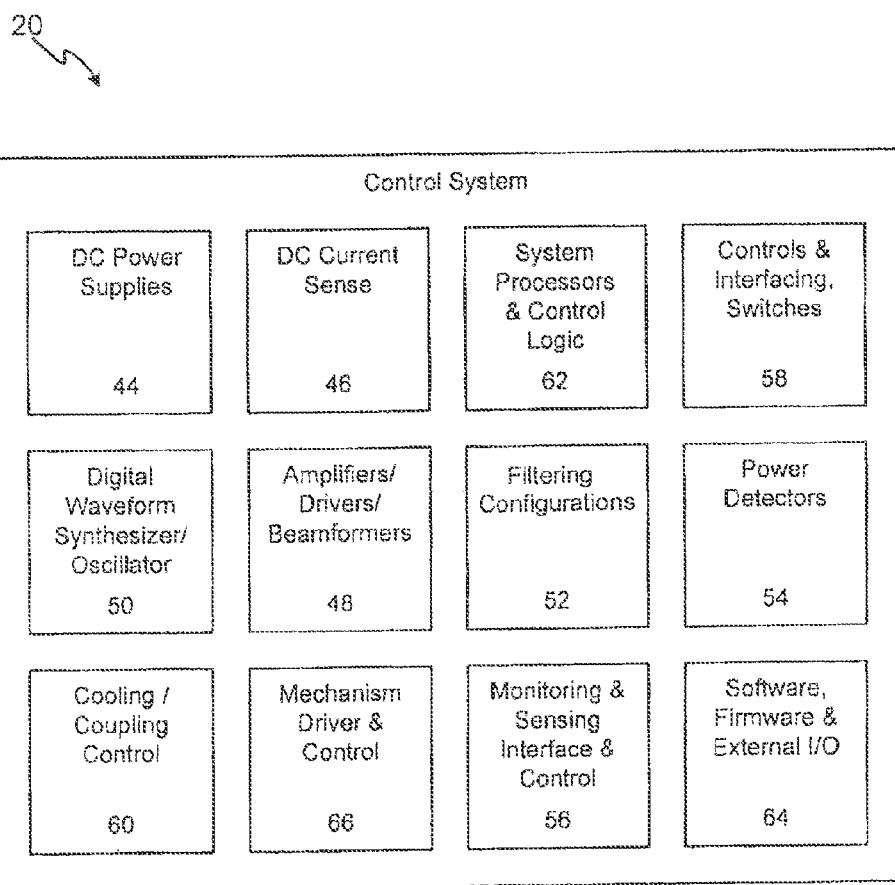

An exemplary transducer is suitably controlled and operated in various manners by control system 20. In an exemplary embodiment depicted in FIGS. 5A-5C, control system 20 is configured for coordination and control of the entire acoustic energy system. For example, control system 20 can suitably comprise power source components 36, sensing and monitoring components 38, cooling and coupling controls 40, and/or processing and control logic components 42. Control system 20 can be configured and optimized in a variety of ways with more or less subsystems and components to enhance therapy, imaging and/or monitoring, and the embodiments in FIGS. 5A and 5B are merely for illustration purposes.

For example, for power sourcing components 36, control system 20 can comprise one or more direct current (DC) power supplies 44 configured to provide electrical energy for entire control system 20, including power required by a transducer electronic amplifier/driver 48. A DC current sense device 46 can also be provided to confirm the level of power going into amplifiers/drivers 48 for safety and monitoring purposes.

Amplifiers/drivers 48 can comprise multi-channel or single channel power amplifiers and/or drivers. In accordance with an exemplary embodiment for transducer array configurations, amplifiers/drivers 48 can also be configured with a beamformer to facilitate array focusing. An exemplary beamformer can be electrically excited by a digitally controlled waveform synthesizer/oscillator 50 with related switching logic.

Power sourcing components 36 can also include various filtering configurations 52. For example, switchable harmonic filters and/or matching may be used at the output of amplifier/driver/beamformer 48 to increase the drive efficiency and effectiveness. Power detection components 54 may also be included to confirm appropriate operation and calibration. For example, electric power and other power detection components 54 may be used to monitor the amount of power going to probe 18.

Various sensing and monitoring components 38 may also be suitably implemented within control system 20. For example, in accordance with an exemplary embodiment, monitoring, sensing, interface and control components 56 may be configured to operate with various motion detection systems implemented within transducer 19 to receive and process information such as acoustic or other spatial and/or temporal information from ROI 12. Sensing and monitoring components 38 can also include various controls, interfacing and switches 58 and/or power detectors 54. Such sensing and monitoring components 38 can facilitate open-loop and/or closed-loop feedback systems within treatment system 14.

In an exemplary embodiment, sensing and monitoring components 38 comprise a sensor that is connected to an audio or visual alarm system to prevent overuse of system 14. In this exemplary embodiment, the sensor senses the amount of energy transferred to stratum corneum 85, viable epidermis 86, viable dermis 88, subcutaneous connective tissue and fat 82, or muscle 84, or the time that system 14 has be actively emitting energy. When a certain time or temperature threshold has been reached, the alarm sounds an audible alarm or causes a visual indicator to activate to alert the user that the threshold is reached. This prevents the user from overusing system 14. In an exemplary embodiment, the sensor could be operatively connected to control system 20 and force control system 20 to stop emitting ultrasound energy 2, 4, 6 and/or 8 from probe 18.

A cooling/coupling control system 60 may be provided to remove waste heat from an exemplary probe 18, provide a controlled temperature at the superficial tissue interface and deeper into tissue, and/or provide acoustic coupling from probe 18 to ROI 12. Such cooling/coupling control system 60 can also be configured to operate in both open-loop and/or closed-loop feedback arrangements with various coupling and feedback components.

Additionally, an exemplary control system 20 can further comprise various system processors and digital control logic 62, such as one or more controls or interfacing switches 58 and associated components, including firmware and software 64, which interfaces to user controls and interfacing circuits as well as input/output circuits and systems for communications, displays, interfacing, storage, documentation, and other useful functions. Software 64 controls all initialization, timing, level setting, monitoring, safety monitoring, and all other system functions required to accomplish user-defined treatment objectives. Further, various mechanisms 66 can also be suitably configured to control operation.

Figure 5C:
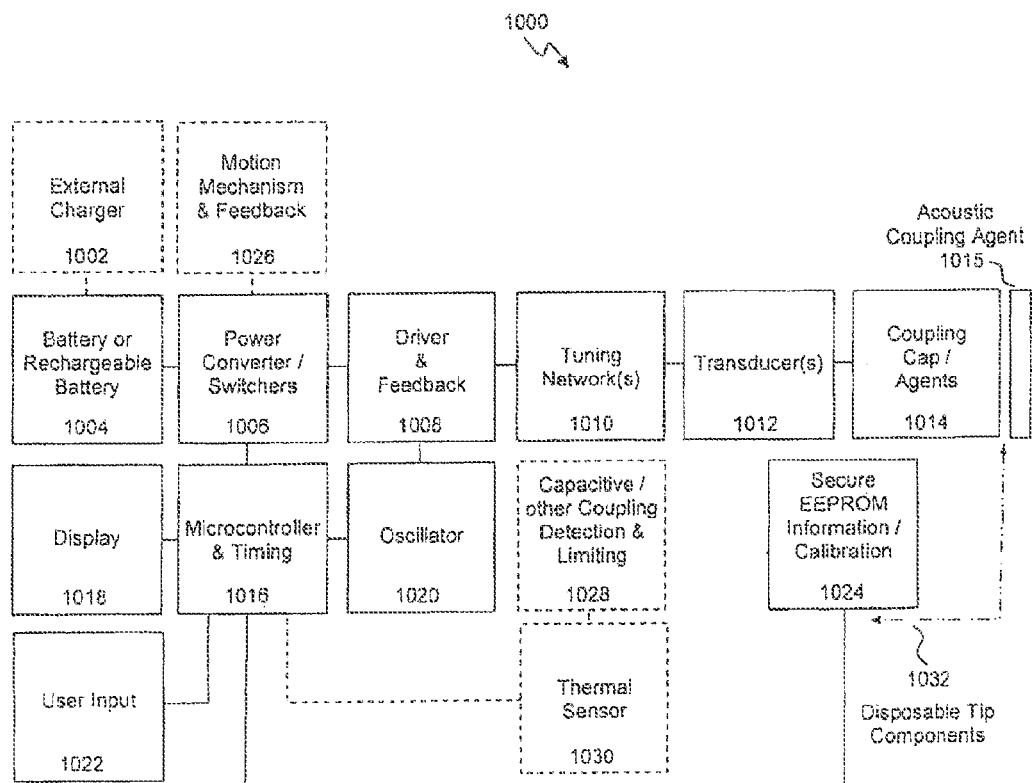

With reference to FIG. 5C, an exemplary transducer is suitably controlled and operated in various manners by a hand-held format control system 1000. An external battery charger 1002 can be used with rechargeable-type batteries 1004 or batteries 1004 can be single-use disposable types, such as AA-sized cells. Power converters 1006 produce voltages suitable for powering a driver/feedback circuit 1008 with tuning network 1010 driving a transducer 1012 coupled to the patient via one or more fluid filled or gel couples. In some embodiments, a fluid filled or gel couple is coupled to the patient with an acoustic coupling agent 1015. In addition, a microcontroller and timing circuits 1016 with associated software and algorithms provide control and user interfacing via a display 1018, oscillator 1020, and other input/output controls 1022 such as switches and audio devices. A storage element 1024, such as an EEPROM, secure EEPROM, tamper-proof EEPROM, or similar device holds calibration and usage data. A motion mechanism with feedback 1026 can be suitably controlled to scan the transducer, if desirable, in a line or two-dimensional pattern and/or with variable depth. Other feedback controls include a capacitive, acoustic, or other coupling detection means and/or limiting controls 1028 and thermal sensor 1030. A combination of the secure EEPROM with at least one of a fluid filled or gel couple, transducer 1012, thermal sensor 1030, coupling detectors 1028, or tuning network 1010 along with a plastic or other housing can comprise a disposable tip 1032.

With reference again to FIG. 3, an exemplary system 14 also includes display system 22 to provide images of the ROI 12 in certain exemplary embodiments wherein ultrasound energy is emitted from transducer 19 in a manner suitable for imaging. Display system can be any type of system that conveys images or information apart from images about system 14 or ROI 12 to the user. Therefore, display system 22 can be a computer monitor, television screen or it can be a simply type of indicator system such a liquid crystal display or light emitting diode display in various exemplary embodiments. Liquid crystal displays and light emitting diode displays are particularly useful when system 14 is a hand-held system.

Display system 22 enables the user to facilitate localization of the treatment area and surrounding structures, e.g., identification of cell membranes or tissues. After localization, delivery of ultrasound energy 2, 4, 6 and/or 8 at a depth, distribution, timing, and energy level is provided, to achieve the desired therapy, imaging and/or monitoring. Before, during, and/or after therapy, i.e., before, during and/or after delivery of ultrasound energy, monitoring of the treatment area and surrounding structures can be conducted to further plan and assess the results and/or provide feedback to control system 20 and a system operator via display system 22. In accordance with an exemplary embodiment, localization can be facilitated through ultrasound imaging that can be used to define an ROI 12 within one or more layers of skin tissue.

For ultrasound energy delivery, transducer 19 can be mechanically and/or electronically scanned to place treatment zones over an extended area in ROI 12. A treatment depth can be adjusted between a range of approximately 1 to 100 millimeters, and/or the greatest depth of muscle 84. Such delivery of energy can occur through imaging of the targeted cell membrane or tissue and then applying ultrasound energy, or application of ultrasound energy at known depths over an extended area without initial or ongoing imaging.

The ultrasound beam from transducer 19 can be spatially and/or temporally controlled by changing the spatial parameters of transducer 19, such as the placement, distance, treatment depth and transducer 19 structure, as well as by changing the temporal parameters of transducer 19, such as the frequency, drive amplitude, and timing, with such control handled via control system 20. Such spatial and temporal parameters can also be suitably monitored and/or utilized in open-loop and/or closed-loop feedback systems within ultrasound system 16.

In accordance with another exemplary embodiment of the present invention, with reference again to FIG. 3, an exemplary monitoring method may comprise monitoring the temperature profile or other tissue parameters of ROI 12, such as attenuation, speed of sound, or mechanical properties such as stiffness and strain of the treatment region and suitably adjust the spatial and/or temporal characteristics and energy levels of ultrasound energy 2, 4, 6 and/or 8 emitted from transducer 19. The results of such monitoring techniques may be indicated on display system 22 by means of one-, two-, or three-dimensional images of monitoring results, or may simply comprise a success or fail-type indicator, or combinations thereof. Additional treatment monitoring techniques may be based on one or more of temperature, video, profilometry, and/or stiffness or strain gauges or any other suitable sensing technique.

Any amount of energy can be used as long as the tissue within ROI 12 is not ablated or coagulated. In an exemplary embodiment, the energy emitted from probe 18 is unfocused or defocused ultrasound energy 2, 4, 6 and/or 8. Alternatively, focused ultrasound energy 2, 4, 6 and/or 8 could be emitted from probe 18 and applied to ROI 12.

In certain exemplary embodiments, system 14 is equipped with certain features to aid the user. One feature is a disposable tip that covers probe 18 during use. The disposable tip enables ultrasound energy 2, 4, 6, and/or 8 to pass through the tip and contact the patient. But, the disposable tip can be removed from probe 18 after use and replaced with a new disposable tip to prevent the spread of germs from one patient to another that might reside on probe 18 after contact with a patient's stratum corneum 85. Different size disposable tips can be used and fall within the scope of the present invention.

In one exemplary embodiment, the energy released into ROI 12 increases the local temperature within ROI 12 from approximately 1°-25° C. over a body's normal temperature. Therefore the temperature within ROI 12 during treatment is between approximately 35°-60° C. In another exemplary embodiment, the temperature is raised approximately 1°-15° C. over a body's normal temperature. Therefore, in this embodiment, the temperature within ROI 12 is between approximately 35°-49° C. While specific temperature ranges are disclosed herein, it should be noted that any temperature is considered to fall within the scope of the present invention.

In certain embodiments, the temperature increase may be very high but applied for a short enough time period so that the energy delivered to ROI 12 does not cause tissue ablation or coagulation. In other situations, the temperature increase may be fairly small and applied long enough to have an effect without causing tissue ablation or coagulation.

The time-temperature profile can be modeled and optimized with the aid of the thermal dose concept. The thermal dose, or $t_{43}$, is the exposure time at 43° C. which causes an equivalent biological effect due to an arbitrary time-temperature heating profile. Typically an ablative lesion forms on the order of one second at 56° C., which corresponds to a thermal dose of one hundred and twenty minutes at 43° C. The same thermal dose corresponds to 50° C. for approximately one minute. Thus a non-ablative profile can contain high temperatures for very short times and/or lower temperatures for longer times or a combination of various time-temperature profiles. For example, temperatures as high as 56° C. for under one second or 46° C. for under fifteen minutes can be utilized. Such processes can be implemented in various exemplary embodiments, whereby one or more profiles may be combined into a single treatment.

In an exemplary embodiment the temperature at ROI 12 is raised to a high level, such as approximately 50° C. or more and held for several seconds. In another exemplary embodiment, the temperature is raised to a high level, (for example greater than 50° C.), for under one second up to five seconds or more, and then turned off for under one second up to five seconds or more, and repeated to create a pulsed profile.

In another exemplary embodiment, the temperature is raised quickly to a high level (greater than 50° C.), and then dropped to a lower temperature (less than 50° C.), and then maintained at that temperature for a given time period such as one second up to several seconds or over a minute.

In another exemplary embodiment, the temperature is increased quickly to a high level ($T_{HIGH}$), whereby $T_{HIGH}$ is greater than 40° C., and the power to system 14 is turned off, but turned on again once the temperature drops below a lower threshold, ($T_{LOW}$), whereby $T_{LOW}$ is less than $T_{HIGH}$. Once the temperature reaches $T_{HIGH}$ again power to system 14 is turned back off and this process is repeated, in effect acting like a thermostat. The process is terminated after a total treatment time of under one second to one minute or more.

In another exemplary embodiment, the temperature is raised quickly to a high level ($T_{START}$), whereby $T_{START}$ is greater than 40° C. and then turned off, but turned on again before the temperature drops appreciably (i.e. by a few degrees) below $T_{START}$, whereby the temperature may then increase a small amount (i.e. by a few degrees) over $T_{START}$ before the power is turned off again. In such an exemplary embodiment the temperature quickly reaches a starting point and then may be allowed to increase to a higher temperature yet still remain in a non-ablative or coagulative regime before the treatment is ended.

The present invention may be described herein in terms of various functional components and processing steps. It should be appreciated that such components and steps may be realized by any number of hardware components configured to perform the specified functions. For example, the present invention may employ various medical treatment devices, visual imaging and display devices, input terminals and the like, which may carry out a variety of functions under the control of one or more control systems or other control devices. In addition, the present invention may be practiced in any number of medical contexts and that the exemplary embodiments relating to a system as described herein are merely indicative of exemplary applications for the invention. For example, the principles, features and methods discussed may be applied to any medical application. Further, various aspects of the present invention may be suitably applied to other applications, such as other medical or industrial applications.

We claim:

1. A system for steering a medicant through a tissue, the tissue having a first region located at a first depth and a second region adjacent to the first region and located at a second depth, the system comprising:
    a probe configured to output a first acoustic energy and a second acoustic energy; and
    a control system coupled to the probe and having a control logic configured to control the output of acoustic energy from the probe, the probe and the control system configured to, in use when the medicant is present in the first region, focus the first acoustic energy from the source to the first region, the first acoustic energy having a first spatial and temporal energy profile configured to provide cavitation and radiation force, the cavitation and radiation force configured to move the medicant from the first region to the second region, the probe and the control system further configured to, in use when the medicant has moved from the first region to the second region, focus the second acoustic energy from the source to the second region, the second acoustic energy having a second spatial and temporal energy profile configured to enhance effectiveness of the medicant in the second region.

2. The system of claim 1, wherein the probe is further configured for ultrasound imaging, ultrasound monitoring, or a combination thereof.

3. The system of claim 1, wherein the probe is configured to output acoustic energy in a frequency range of 1 kHz to 500 MHz.

4. The system of claim 1, wherein the probe is configured to output acoustic energy in a frequency range of 200 kHz to 20 MHz.

5. The system of claim 1, wherein the medicant is a chemical naturally occurring within the body.

6. The system of claim 5, wherein the chemical is selected from the group consisting of a cell, an amino acid, a protein, an antibody, a mineral, and a vitamin.

7. The system of claim 1, wherein enhancing the effectiveness of the medical comprises increasing permeability or transparency of the medicant in the tissue with the second acoustic energy.

8. The system of claim 1, wherein enhancing the effectiveness of the medicant comprises creating a thermal effect in said tissue with said second acoustic energy.

9. A system for delivering a medicant to a region of interest within a tissue, the tissue having a first region located at a first depth, the region of interest located adjacent to the first region and at a second depth, the system comprising:
    a probe configured to output a first acoustic energy and a second acoustic energy; and
    a control system coupled to the probe and having a control logic configured to control the output of acoustic energy from the probe, the probe and the control system configured to, in use when a medicant is present in the first region, focus the first acoustic energy from the source to the first region, the first acoustic energy having a first spatial and temporal energy profile configured to provide cavitation and radiation force, the cavitation and radiation force configured to move the medicant from the first region to the second region, the probe and the control system further configured to, in use when the medicant has moved from the first region to the region of interest, focus the second acoustic energy from the source to the region of interest, the second acoustic energy having a second spatial and temporal energy profile configured to provide a thermal effect that enhances the effectiveness of the medicant in the region of interest.

10. The system of claim 9, wherein the probe is further configured for ultrasound imaging, ultrasound monitoring, or a combination thereof.

11. The system of claim 9, wherein the probe is configured to output acoustic energy in a frequency range of 1 kHz to 500 MHz.

12. The system of claim 9, wherein the probe is configured to output acoustic energy in a frequency range of 200 kHz to 20 MHz.

13. The system of claim 9, wherein the medicant is a chemical naturally occurring within the body.

14. The system of claim 13, wherein the chemical is selected from the group consisting of a cell, an amino acid, a protein, an antibody, a mineral, and a vitamin.

15. A system for delivering a medicant to a portion of skin beneath a stratum corneum, the system comprising:
    a probe configured to output a first acoustic energy and a second acoustic energy; and
    a control system coupled to the probe and having a control logic configured to control the output of acoustic energy from the probe, the probe and the control system configured to, in use when a medicant is present on a surface of the stratum corneum, focus the first acoustic energy from the source to a first depth beneath the stratum corneum, the first acoustic energy having a first spatial and temporal energy profile configured to provide a first cavitation and radiation force, the first cavitation and radiation force configured to deliver the medicant across the stratum corneum to the first depth beneath the stratum corneum, the probe and the control system further configured to, in use when the medicant has been delivered to the first depth beneath the stratum corneum, focus the second acoustic energy from the source to a second depth beneath the stratum corneum, the second acoustic energy having a second spatial and temporal energy profile configured to provide a second cavitation and radiation force, the second cavitation and radiation force configured to move the medicant from the first depth to the second depth, and wherein the second spatial and temporal energy profile is different from the first spatial and temporal enemy profile.

16. The system of claim 15, wherein the probe is further configured to output a third acoustic energy, the probe and the control system further configured to, in use when the medicant has been moved from the first depth beneath the stratum corneum to the second depth beneath the stratum corneum, focus the third acoustic energy from the source to the second depth beneath the stratum corneum, the third acoustic energy having a third spatial and temporal energy profile configured to activate the medicant.

17. The system of claim 16, wherein activating the medicant comprises creating a thermal effect in said tissue with said third acoustic energy from said source.

18. The system of claim 15, wherein the probe is further configured for ultrasound imaging, ultrasound monitoring, or a combination thereof.

19. The system of claim 15, wherein the probe is configured to output acoustic energy in a frequency range of 1 kHz to 500 MHz.

20. The system of claim 15, wherein the probe is configured to output acoustic energy in a frequency range of 200 kHz to 20 MHz.

* * * * *

UNITED STATES PATENT AND TRADEMARK OFFICE
CERTIFICATE OF CORRECTION

PATENT NO. : 9,907,942 B2
APPLICATION NO. : 14/868923
DATED : March 6, 2018
INVENTOR(S) : Michael H. Slayton et al.

Page 1 of 1

It is certified that error appears in the above-identified patent and that said Letters Patent is hereby corrected as shown below:

In the Claims

Column 14, Claim 15, Line 58, "enemy" should be --energy--.

Signed and Sealed this
Sixteenth Day of July, 2019

Andrei Iancu
*Director of the United States Patent and Trademark Office*